United States Patent
Lou et al.

(10) Patent No.: US 10,365,340 B1
(45) Date of Patent: Jul. 30, 2019

(54) MONITORING DYNAMICS OF PATIENT BRAIN STATE DURING NEUROSURGICAL PROCEDURES

(71) Applicant: Siemens Medical Solutions USA, Inc., Malvern, PA (US)

(72) Inventors: Bin Lou, West Windsor, NJ (US); Francisco Pereira, Jersey City, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 40 days.

(21) Appl. No.: 15/908,948

(22) Filed: Mar. 1, 2018

(51) Int. Cl.
| | |
|---|---|
| *G01V 3/00* | (2006.01) |
| *G01R 33/48* | (2006.01) |
| *A61B 5/055* | (2006.01) |
| *G01R 33/28* | (2006.01) |
| *A61B 34/00* | (2016.01) |
| *A61B 5/06* | (2006.01) |
| *A61B 34/20* | (2016.01) |
| *A61B 90/00* | (2016.01) |
| *A61B 34/10* | (2016.01) |

(52) U.S. Cl.
CPC .......... *G01R 33/4806* (2013.01); *A61B 5/055* (2013.01); *A61B 5/062* (2013.01); *A61B 34/25* (2016.02); *G01R 33/285* (2013.01); *A61B 34/10* (2016.02); *A61B 34/20* (2016.02); *A61B 2090/374* (2016.02)

(58) Field of Classification Search
USPC ........................................................ 324/309
See application file for complete search history.

(56) References Cited

U.S. PATENT DOCUMENTS

| | | | | |
|---|---|---|---|---|
| 9,349,178 | B1* | 5/2016 | Itu | ........................... G16H 50/50 |
| 2013/0211238 | A1* | 8/2013 | DeCharms | ........... A61B 5/4824 600/418 |
| 2014/0148657 | A1* | 5/2014 | Hendler | ............... A61B 5/0476 600/301 |
| 2016/0054409 | A1* | 2/2016 | Wager | .................. A61B 5/4824 600/411 |
| 2018/0143275 | A1* | 5/2018 | Sofka | .................... A61B 5/0042 |
| 2018/0214086 | A1* | 8/2018 | Park | ....................... G06K 9/342 |
| 2018/0228460 | A1* | 8/2018 | Singh | ................... A61B 6/5217 |
| 2019/0011521 | A1* | 1/2019 | Sofka | .................. A61B 5/0042 |
| 2019/0046099 | A1* | 2/2019 | Lee | ....................... A61B 5/0261 |
| 2019/0059780 | A1* | 2/2019 | Lee | ........................ A61B 5/055 |
| 2019/0117072 | A1* | 4/2019 | Pereira | ................. A61B 5/0042 |
| 2019/0120918 | A1* | 4/2019 | Pereira | ............... G01R 33/4806 |

OTHER PUBLICATIONS

Mitchell, T. M. et al. Predicting human brain activity associated with the meanings of nouns. Science 320, 1191-1195 (2008).

\* cited by examiner

*Primary Examiner* — Rodney E Fuller

(57) ABSTRACT

A computer-implemented method of monitoring dynamics of patient brain state during neurosurgical procedures includes receiving a plurality of brain response images acquired using a functional MRI scan of a patient over a plurality of time points and selecting a plurality of image features from the brain response images. One or more recurrent neural network (RNN) model are used to directly estimate one or more brain state measurements at each time point based on the image features. Once estimated, the brain state measurements are presented on a display.

19 Claims, 3 Drawing Sheets

US 10,365,340 B1

MONITORING DYNAMICS OF PATIENT BRAIN STATE DURING NEUROSURGICAL PROCEDURES

TECHNICAL FIELD

The present disclosure relates to monitoring dynamics of patient brain state. The technology described herein is particularly well-suited for, but not limited to, neurosurgical procedures.

BACKGROUND

Intraoperative Magnetic Resonance Imaging (MRI) integrates operative interventions (e.g., intracranial neurosurgical procedures) with MRI for immediate evaluation of cerebral interventions and resections. In conventional functional MRI-guided (fMRI) surgical procedures performed in an MR-operating room (MR-OR), fMRI is used for localizing specific functional areas (e.g., primary motor area or language area) and assessing the proximity to a lesion volume. Typically, neurosurgeons use the fMRI before a surgery to plan the trajectory of the operation, but the brain state might vary dynamically or the brain can shift before the actual surgery takes place, which makes that fMRI image inaccurate. Also, neurosurgeons often rely on patients to be awake during operations to providing behavior cues. It is beneficial to simultaneously monitor patients' cognitive state directly from functional images.

Accordingly, it is desired to provide a real-time fMRI guidance system that can show a brain activation map related to certain cognitive tasks in real time while also identifying regions of interests (ROIs) associated with specific cognitive or behavioral functions as well as locations that indicate patient pain, craving, attention, or other quantities driving the neuro-feedback process. Additionally, such a system should be capable of extracting quantitative measurements of brain state and simultaneously decoding patient characteristics in real time to allow brain response for a specific operational event (encoding models) to be predicted.

SUMMARY

Embodiments of the present invention address and overcome one or more of the above shortcomings and drawbacks, by providing methods, systems, and apparatuses related to monitoring patient brain state dynamics during neurosurgical procedures.

According to some embodiments, a computer-implemented method of monitoring dynamics of patient brain state during neurosurgical procedures includes receiving a plurality of brain response images acquired using a functional MRI scan of a patient over a plurality of time points and selecting a plurality of image features from the brain response images. One or more recurrent neural network (RNN) models are used to directly estimate one or more brain state measurements at each time point based on the image features. Once estimated, the brain state measurements are presented on a display.

In some embodiments, the image features in the aforementioned method are selected by applying one or more 3D convolutional networks to the brain response images. In other embodiments, the image features are selected from the brain response images using an informativeness-based voxel selection method. This informativeness-based voxel selection method may be applied to a subset of the voxels in each brain response image remaining after applying a cortical mask to each brain response image. For example, in one embodiment, the subset of the voxels in each brain response image comprises approximately 10% voxels in each brain response image. In some embodiments, the informativeness-based voxel selection method determines an informativeness score for each voxel in the subset of the voxels by applying one or more ridge regression models to predict one or more dimensions of the brain state measurements from each voxel and its adjacent neighbors in 3D.

In some embodiments of the aforementioned method, the RNN models comprise (a) a first layer long short-term memory (LSTM) model receiving the image features and generating internal output data and (b) a second layer LSTM model receiving the internal output data and estimating the brain state measurements. In these embodiments, the output of first LSTM is for model internal use only and usually not visible to the outside. Brain state may be the only output of the system. The brain state for a given time point may be used as an input to the second layer LSTM model for subsequent time points.

According to other embodiments of the present invention, a computer-implemented method of monitoring dynamics of patient brain state during neurosurgical procedures includes receiving brain response images collected using a functional MRI scan of a patient over multiple points, and selecting image features from the brain response images. Brain state measurements are estimated at each time point by (a) applying a decoding model that convolves the image features with a canonical hemodynamic response function (HRF) to yield combined features and (b) estimating the brain state measurements as a linear combination of the combined features. A display may then be used to present the brain state measurements.

In other embodiments of the present invention, a system for monitoring dynamics of patient brain state during neurosurgical procedures includes a functional MRI scanner, one or more processors, and a display. The functional MRI scanner acquires brain response images over multiple time points. The processors are configured to (a) select a plurality of image features from the brain response images and (b) apply one or more machine learning models to estimate one or more brain state measurements at each time point based on the image features. The display presents the one or more brain state measurements.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Figure 1:
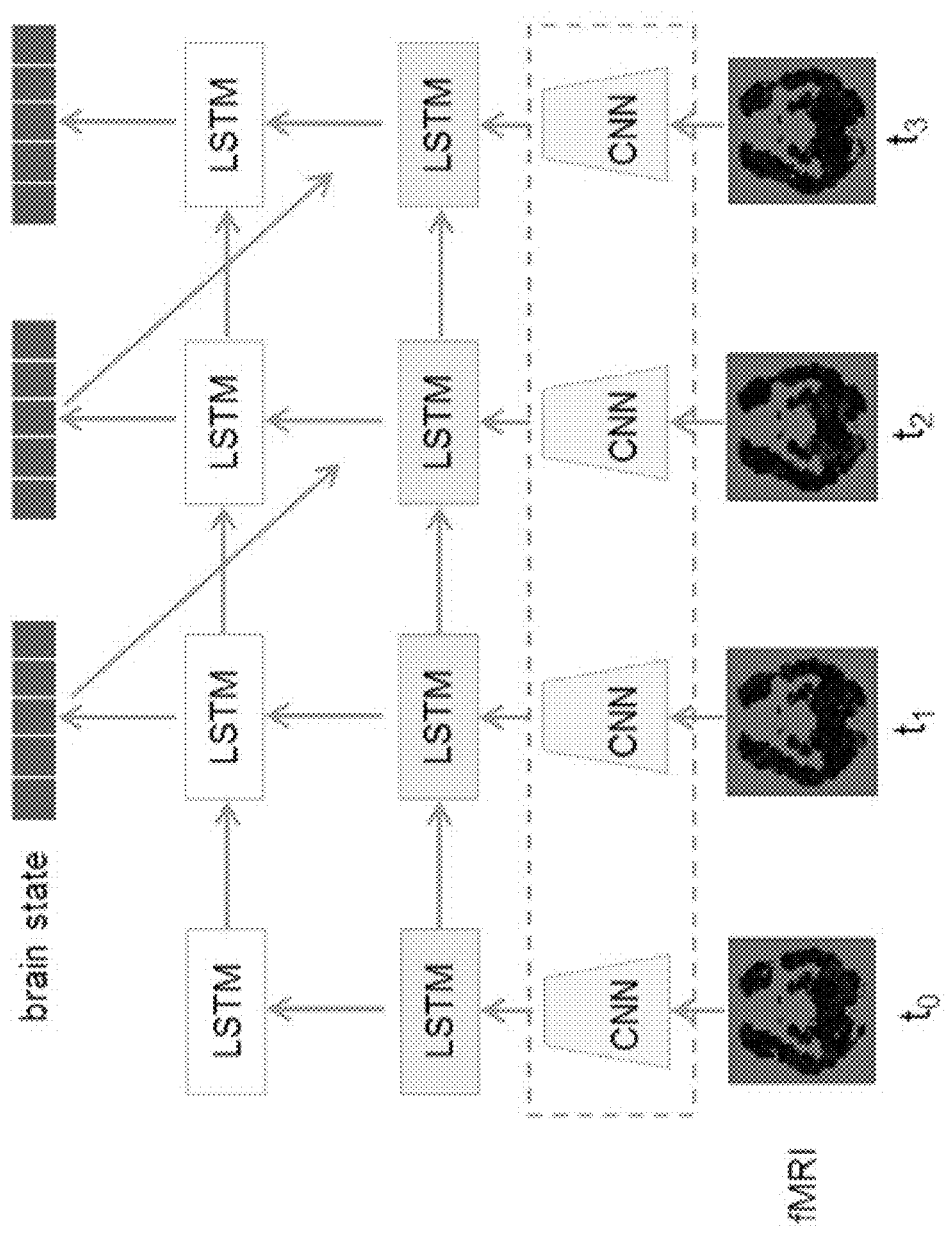
FIG. 1 shows architecture of the LSTM-based decoding models, as they may be applied in some embodiments.

Systems, methods, and apparatuses are described herein which relate generally to monitoring the dynamics of patient brain state during neurosurgical procedures. The techniques described herein address the general problem of identifying the real-time brain state of a patient from fMRI data of the brain, especially acquired during neurosurgical procedures in MR-OR. This is an auxiliary system of intelligent MR scanner and MR compatible operating room for immediate evaluation of cerebral interventions. Other medical imaging systems that require real-time monitoring of patients' characteristics could also use the system, if available. From a high level point of view, this interventional system has the following potential functions distinguished from conventional MRI-based radiomics systems. First, it facilitates the real-time estimation of brain state from fMRI recordings and monitoring of the dynamics of brain activity during neurosurgical procedures. Second, the interventional system disclosed herein supports pre-surgical planning and decision-making by real-time localization of eloquent cortex adjacent to brain lesions. Third, the interventional system predicts the changes of brain activity and provides real-time neurofeedback according to the cognitive state of the patient.

Let $x^t \in \mathbb{R}^n$ be a brain response (e.g., the fMRI image) and $z^t \in \mathbb{R}^m$ be brain state measurements (or patient characteristics) at temporal interval [t, t+1], where n is the number of voxel response and m is the number of measurement dimensions. We are interested in predicting the most likely response $z^t$ given the stimulus history $X^t=(x^0, \ldots, x^t)$:

$$z^t = \arg\max Pr(z^t | X^t) = f(\phi(x^0), \ldots, \phi(x^t))$$

where Pr is a decoding distribution, $\phi$ is a feature model such that $\phi(\bullet) \in \mathbb{R}^p$, p is the number of feature dimensions, and f is a decoding model such that $f(\bullet) \in \mathbb{R}^m$.

In order to solve this problem, the feature model is defined to transform the functional image to features and the decoding model to transform features to responses. Various feature models may be used in this regard. For example, in some embodiments, features (i.e., voxels) are selected based on the voxel "informativeness" in the training dataset. In other embodiments, a feature selection model is trained using 3D convolutional neural network.

Using the informativeness method, the image data is reduced to a subset of the voxels. For example, in one embodiment, the total image data is reduced to a subset of 5,000 voxels, approximately 10% of the number left after applying a cortical mask. For the purposes of this disclosure "approximately 10%" is meant to include values between 9-11% of the voxels. This number is selected as a conservative upper bound for the number of informative voxels, as determined in previous studies. Voxels can be selected by the degree to which they are informative about the brain state measurements for training set images, as measured by ridge regressions on the voxel and its adjacent 3D neighbors. Ridge regression models can be learned (with the regularization parameter set to 1) to predict each brain state dimension from the imaging data of each voxel and its 26 adjacent neighbors in 3D, in cross-validation within the training set. This yields predicted values for each brain state dimension, which may then be correlated with the values in the true brain state measurements. The informativeness score for each voxel is then the maximum for such correlation across dimensions.

After feature extraction, decoding may be performed using a linear method using ridge regression to de-convolve the canonical hemodynamic response. The linear method estimates brain state as a linear combination of image features. The decoding model convolves the features with the canonical hemodynamic response function (HRF) and estimates the brain state measurements as a linear combination of these features:

$$\hat{z}^t = (H_c F_c B)^t$$

where $H_c \in \mathbb{R}^{t \times t}$ is the Toeplitz matrix of the canonical HRF, $F_c = [\phi(x^0), \ldots, \phi(x^t)]^T \in \mathbb{R}^{t \times p}$ is the matrix of features and $B \in \mathbb{R}^{p \times m}$ is the matrix of regression coefficients.

The training set may be used for model estimation (a column of B per brain state dimension). Regularization parameters were optimized by cross-validation. The columns of B are estimated by analytically minimizing the $L^2$-penalized least squares loss function.

$$B = (F_c^T H_c^T H_c F_c + \lambda I)^{-1} F_c^T H_c^T z^t.$$

As an alternative to the linear method, in other embodiments, decoding is performed using a non-linear method using recurrent neural network (RNN) to model the hemodynamic response for each patient and directly estimate the brain state at each time point. The RNN model uses its internal memories for nonlinearly processing arbitrary feature sequences and predicting feature-evoked responses as a linear combination of their second-layer hidden states:

$$z^t = h_2^t W^t$$

where $h_2^t$ represents the hidden states in the second layer (e.g., the output of upper LSTM layer in FIG. 1), and W are the weights (e.g., the arrow between upper LSTM layer and brain state output in FIG. 1). W is usually an m-by-k matrix where m is the number of different brain states we want to decode and k, the number of output units of the hidden layer. This linear transformation can be implemented through a fully connected layer, and the weights, W, can be trained with other RNN parameters all together. The RNN models differ in the type and number of artificial neurons.

The RNN models may differ in type and number of artificial neurons. For example, as would be understood by one skilled in the art, a RNN is a more general term for time dependent networks. A long short-term memory (LSTM) model is a special kind of RNN which is capable of learning long-term dependencies. Thus, in some embodiments, a LSTM architecture may be used, in which the first-layer hidden states of an LSTM unit (lower LSTM layer in FIG. 1) are defined as:

$$h^t = o^t \odot \tanh(c^t)$$

$$o^t = \sigma(U_O h^{t-1} + W_O \phi(x^t) + b_O)$$

where $\odot$ denotes element-wise multiplication, $c^t$ is the cell state, and $o^t$ are the output gate activities. The cell state maintains information about the previous time points.

An example architecture of the LSTM-based decoding models is shown in FIG. 1. The dashed line box indicates 3D convolution networks for feature selection. In some embodiments, this part is replaced by informativeness based voxel selection method to simplify the model if there is strong prior knowledge of the activation patterns or the system only has a limited amount of training data.

Both ridge regression-based and RNN-based decoding methods can effectively model the hemodynamic response.

However, in the ridge regression models, the brain state at each time point is estimated independently after de-convolved with HRF. This method lacks the consideration of temporal dependencies of brain state. Contrarily, RNN models can use their internal memories to capture the temporal dependencies in the data. In the context of modeling the dynamics of brain state, these dependencies can be caused by either neurovascular coupling or by event-induced cognitive processes.

Figure 2:
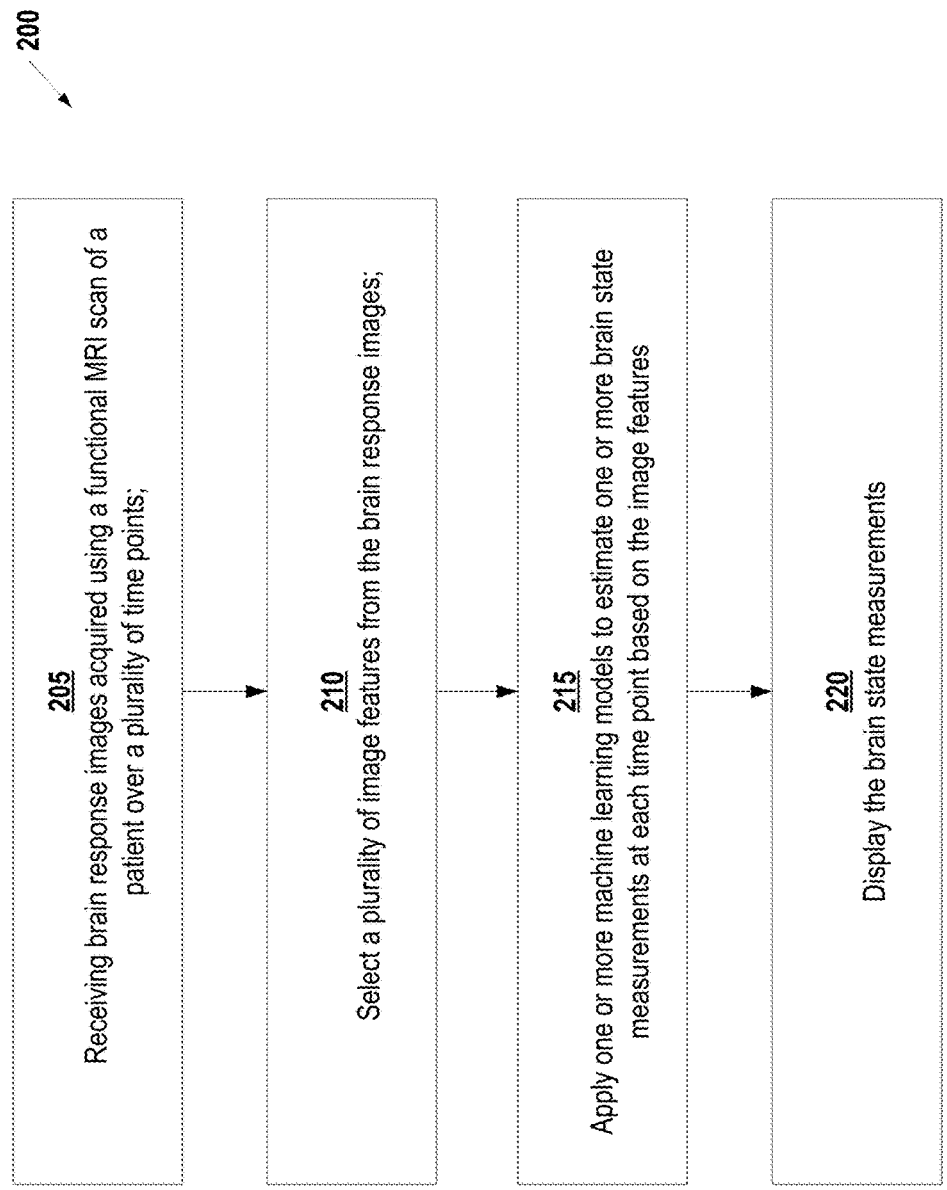
FIG. 2 illustrates a computer-implemented method for monitoring dynamics of patient brain state during neurosurgical procedures, according to some embodiments.

FIG. 2 illustrates a computer-implemented method 200 for monitoring dynamics of patient brain state during neurosurgical procedures, according to some embodiments. Starting at step 205, a plurality of brain response images collected are acquired using a functional MRI scan of a patient over a plurality of time points. In some embodiments, rather than collecting images in real-time, previously acquired images may be loaded from one or more computer-readable mediums.

At step 210, a plurality of image features are selected from the brain response images. In some embodiments, the image features are selected by applying one or more 3D convolutional networks to the plurality of brain response images. In other embodiments, the image features are selected from the brain response images using an informativeness-based voxel selection method. For example, in one embodiment, the informativeness-based voxel selection method is applied to a subset of the voxels in each brain response image remaining after applying a cortical mask to each brain response image. As discussed above, in some embodiments, the subset of the voxels in each brain response image comprises approximately 10% voxels in each brain response image. The informativeness-based voxel selection method may determine an informativeness score for each voxel in the subset of the voxels, for example, by applying ridge regression models to predict one or more dimensions of the brain state measurements from each voxel and its adjacent neighbors in 3D.

One or more machine learning models are used at step 215 to directly estimate one or more brain state measurements at each time point based on the image features. In some embodiments, these machine learning models are LSTM models. For example, in one embodiment, these LSTM models comprise (a) a first layer LSTM model receiving the plurality of image features and generating output data and (b) a second layer LSTM model receiving the output data and estimating the one or more brain state measurements. In one embodiment, as shown in FIG. 1, the brain state for a given time point is used as an input to the second layer LSTM model for subsequent time points. As an alternative to using LSTMs, in some embodiments, the brain state measurements are estimated at each time point by (a) applying a decoding model that convolves the image features with a canonical hemodynamic response function (HRF) to yield combined features and (b) estimating the brain state measurements as a linear combination of the combined features. Finally, at step 220, the one or more brain state measurements are displayed, for example, on a monitor in a surgical setting. For example, the brain monitoring device can display indices of hypnosis that allows for immediate assessments of anesthetics impact on consciousness and providing alerts if the brain state is out of normal range.

The system described herein envisions that intraoperative fMRI will become an indispensable tool for determining the location of a functional area of concern in reference to a targeted lesion and real-time monitoring of the brain state is crucial to the success of neurosurgery. From this perspective, it would greatly increase the utilization and demand for intraoperative MRI scanners. For example, this brain state monitoring system can be embedded into the current Siemens MAGNETOM Combi Suite Neurosurgery system to help neurosurgeons more accurately diagnose and treat patients and improve the outcome and clinician confidence of all surgeries performed. Furthermore, this brain state monitoring system could be adopted by any product that needs a real-time estimation of the dynamic response of the patient from image/non-image data.

Figure 3:
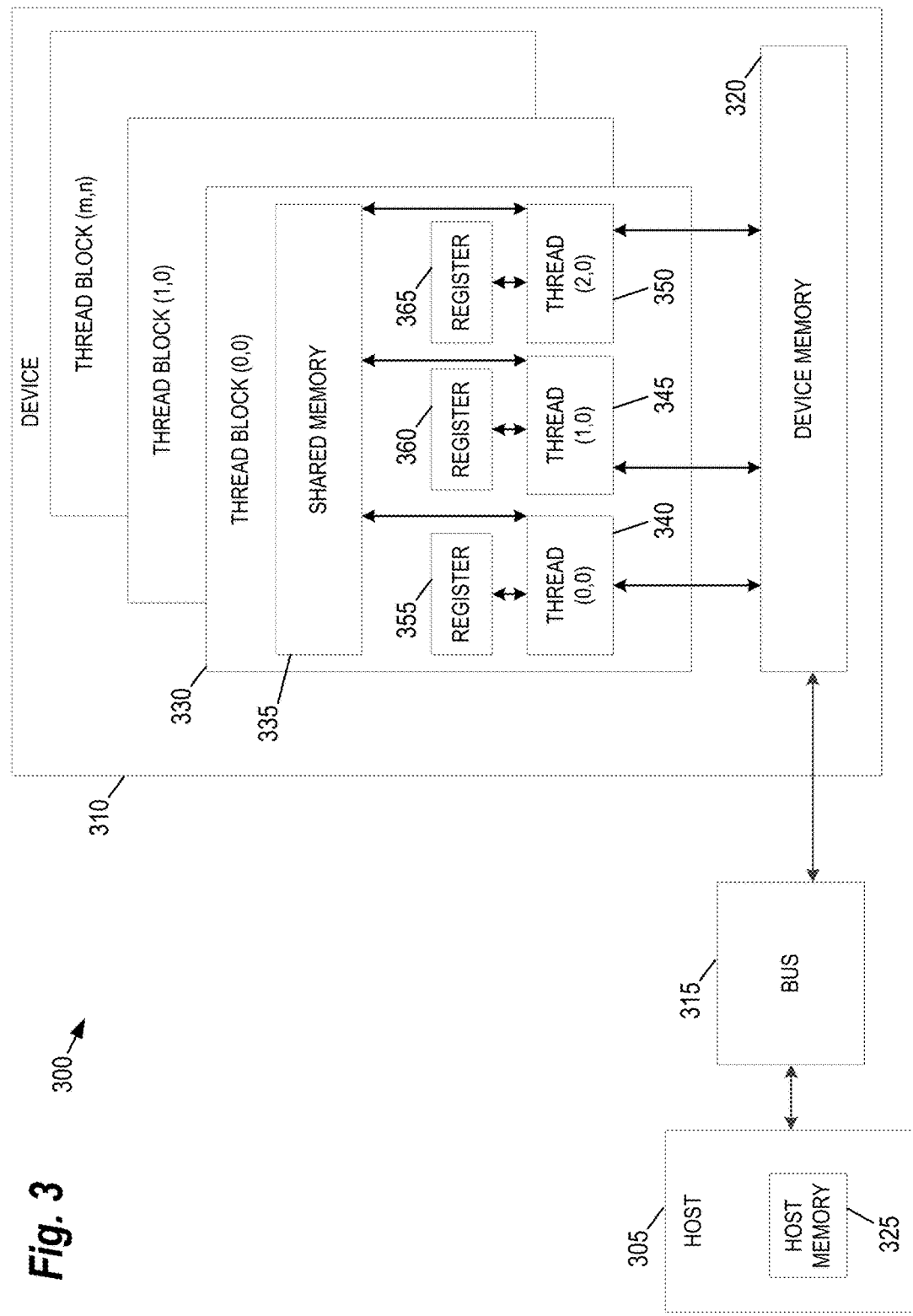
FIG. 3 provides an example of a parallel processing memory architecture that may be utilized to perform com-

FIG. 3 provides an example of a parallel processing memory architecture 300 that may be utilized by to perform computations related to execution of the algorithms discussed herein, according to some embodiments of the present invention. This architecture 300 may be used in embodiments of the present invention where NVIDIA™ CUDA (or a similar parallel computing platform) is used. The architecture includes a host computing unit ("host") 305 and a GPU device ("device") 310 connected via a bus 315 (e.g., a PCIe bus). The host 305 includes the central processing unit, or "CPU" (not shown in FIG. 3) and host memory 325 accessible to the CPU. The device 310 includes the graphics processing unit (GPU) and its associated memory 320, referred to herein as device memory. The device memory 320 may include various types of memory, each optimized for different memory usages. For example, in some embodiments, the device memory includes global memory, constant memory, and texture memory.

Parallel portions of a deep learning application may be executed on the architecture 300 as "device kernels" or simply "kernels." A kernel comprises parameterized code configured to perform a particular function. The parallel computing platform is configured to execute these kernels in an optimal manner across the architecture 300 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below). Using concurrent kernel execution, streams, and synchronization with lightweight events, the architecture 300 of FIG. 3 (or similar architectures) may be used to parallelize training of a deep neural network. For example, in some embodiments, the training dataset is partitioned such that multiple kernels execute the LSTM models simultaneously on subsets of the training data.

The device 310 includes one or more thread blocks 330 which represent the computation unit of the device 310. The term thread block refers to a group of threads that can cooperate via shared memory and synchronize their execution to coordinate memory accesses. For example, in FIG. 3, threads 340, 345 and 350 operate in thread block 330 and access shared memory 335. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 3, the thread blocks 330 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. In some embodiments, processing of subsets of the training data or operations performed by the algorithms discussed herein may be partitioned over thread blocks automatically by the parallel computing platform software. However, in other embodiments, the individual thread blocks can be selected and configured to optimize training of the machine learning models described herein. For example, in one embodiment, each thread block is assigned a subset of training data for a particular region of the brain.

Continuing with reference to FIG. 3, registers 355, 360, and 365 represent the fast memory available to thread block 330. Each register is only accessible by a single thread. Thus, for example, register 355 may only be accessed by thread 340. Conversely, shared memory is allocated per thread block, so all threads in the block have access to the same shared memory. Thus, shared memory 335 is designed to be accessed, in parallel, by each thread 340, 345, and 350 in thread block 330. Threads can access data in shared memory 335 loaded from device memory 320 by other threads within the same thread block (e.g., thread block 330). The device memory 320 is accessed by all blocks of the grid and may be implemented using, for example, Dynamic Random-Access Memory (DRAM).

Each thread can have one or more levels of memory access. For example, in the architecture 300 of FIG. 3, each thread may have three levels of memory access. First, each thread 340, 345, 350, can read and write to its corresponding registers 355, 360, and 365. Registers provide the fastest memory access to threads because there are no synchronization issues and the register is generally located close to a multiprocessor executing the thread. Second, each thread 340, 345, 350 in thread block 330, may read and write data to the shared memory 335 corresponding to that block 330. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 310 to read and/or write to the device memory. Device memory requires the longest time to access because access must be synchronized across the thread blocks operating on the device. Thus, in some embodiments, the processing of each seed point is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 3, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

Various types of fMRI scanners exist and, in general, any such scanner known in the art may be used in conjunction with the techniques described herein. One example system is described in U.S. Pat. No. 20140,180,060 to Parrish et al., issued Jun. 26, 2014, entitled "Methods and Systems for Automated Functional MRI in Clinical Applications," the entirety of which is incorporated herein by reference.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

The invention claimed is:

1. A computer-implemented method of monitoring dynamics of patient brain state during neurosurgical procedures, the method comprising:
   receiving a plurality of brain response images acquired using a functional MRI (fMRI) scan of a patient over a plurality of time points;

selecting a plurality of image features from the brain response images;
using one or more recurrent neural network (RNN) models to directly estimate one or more brain state measurements at each time point based on the image features; and
presenting the one or more brain state measurements on a display.

2. The method of claim 1, wherein the plurality of image features are selected by applying one or more 3D convolutional networks to the plurality of brain response images.

3. The method of claim 1, wherein the plurality of image features are selected from the brain response images using an informativeness-based voxel selection method.

4. The method of claim 3, wherein the informativeness-based voxel selection method is applied to a subset of the voxels in each brain response image remaining after applying a cortical mask to each brain response image.

5. The method of claim 4, wherein the subset of the voxels in each brain response image comprises approximately 10% voxels in each brain response image.

6. The method of claim 4, wherein the informativeness-based voxel selection method determines an informativeness score for each voxel in the subset of the voxels by applying one or more ridge regression models to predict one or more dimensions of the brain state measurements from each voxel and its adjacent neighbors in 3D.

7. The method of claim 1, wherein the one or more RNN models comprise (a) a first layer long short-term memory (LSTM) model receiving the plurality of image features and generating internal output data and (b) a second layer LSTM model receiving the internal output data and estimating the one or more brain state measurements.

8. The method of claim 7, wherein the brain state for a given time point is used as an input to the second layer LSTM model for subsequent time points.

9. A computer-implemented method of monitoring dynamics of patient brain state during neurosurgical procedures, the method comprising:
receiving a plurality of brain response images collected using a functional MRI scan of a patient over a plurality of time points;
selecting a plurality of image features from the brain response images;
estimating one or more brain state measurements at each time point by (a) applying a decoding model that convolves the image features with a canonical hemodynamic response function (HRF) to yield combined features and (b) estimating the brain state measurements as a linear combination of the combined features; and
presenting the one or more brain state measurements on a display.

10. The method of claim 9, wherein the plurality of image features are selected by applying one or more 3D convolutional networks to the plurality of brain response images.

11. The method of claim 9, wherein the plurality of image features are selected from the brain response images using an informativeness-based voxel selection method.

12. The method of claim 11, wherein the informativeness-based voxel selection method is applied to a subset of the voxels in each brain response image remaining after applying a cortical mask to each brain response image.

13. The method of claim 12, wherein the subset of the voxels in each brain response image comprises approximately 10% voxels in each brain response image.

14. The method of claim 12, wherein the informativeness-based voxel selection method determines an informativeness score for each voxel in the subset of the voxels by applying one or more ridge regression models to predict one or more dimensions of the brain state measurements from each voxel and its adjacent neighbors in 3D.

15. The method of claim 9, wherein the brain state measurements are estimated using one or more RNN models comprising (a) a first layer LSTM model receiving the plurality of image features and generating output data and (b) a second layer LSTM model receiving the output data and estimating the one or more brain state measurements.

16. The method of claim 15, wherein the brain state for a given time point is used as an input to the second layer LSTM model for subsequent time points.

17. A system for monitoring dynamics of patient brain state during neurosurgical procedures, the system comprising:
a functional MRI scanner configured to acquire a plurality of brain response images over a plurality of time points;
one or more processors configured to (a) select a plurality of image features from the brain response images and (b) apply one or more machine learning models to estimate one or more brain state measurements at each time point based on the image features;
a display configured to present the one or more brain state measurements.

18. The system of claim 17, wherein the one or more brain state measurements are estimated by:
using one or more long short-term memory (LSTM) models to directly estimate one or more brain state measurements at each time point based on the image features.

19. The system of claim 17, wherein the one or more brain state measurements are estimated by:
estimating one or more brain state measurements at each time point by (a) applying a decoding model that convolves the image features with a canonical hemodynamic response function (HRF) to yield combined features and (b) estimating the brain state measurements as a linear combination of the combined features.

* * * * *